(12) United States Patent
Smith et al.

(10) Patent No.: US 6,846,301 B2
(45) Date of Patent: Jan. 25, 2005

(54) DISPOSABLE SAFETY SYRINGE

(75) Inventors: Martin E. Smith, Camarillo, CA (US); Thomas R. Coughlin, Jr., Tulsa, OK (US); Earl R. Boyer, Simi Valley, CA (US); Stuart J. Daley, Camarillo, CA (US)

(73) Assignee: Maxxon, Inc., Tulsa, OK (US)

( * ) Notice: Subject to any disclaimer, the term of this patent is extended or adjusted under 35 U.S.C. 154(b) by 159 days.

(21) Appl. No.: 10/285,904

(22) Filed: Nov. 1, 2002

(65) Prior Publication Data

US 2004/0087907 A1 May 6, 2004

(51) Int. Cl.[7] .......................... A61M 5/00; A61M 5/315
(52) U.S. Cl. ........................................ 604/110; 604/236
(58) Field of Search ............................... 604/110, 228, 604/240, 195, 192, 198, 236–238

(56) References Cited

U.S. PATENT DOCUMENTS

| | | |
|---|---|---|
| 4,425,120 A | 1/1984 | Sampson et al. |
| 4,643,200 A | 2/1987 | Jennings, Jr. |
| 4,675,005 A | 6/1987 | DeLuccia |
| 4,692,156 A | 9/1987 | Haller |
| 4,747,830 A | 5/1988 | Gloyer et al. |
| 4,790,822 A | 12/1988 | Haining |
| 4,816,022 A | 3/1989 | Poncy |
| 4,908,022 A | 3/1990 | Haber |
| 5,000,736 A | 3/1991 | Kaufhold et al. |
| 5,885,257 A | 3/1999 | Badger |
| 6,193,695 B1 | 2/2001 | Rippstein, Jr. |
| 6,458,105 B1 * | 10/2002 | Rippstein et al. ........... 604/195 |
| 2003/0212371 A1 * | 11/2003 | Smith et al. ................ 604/229 |

* cited by examiner

Primary Examiner—Sharon Kennedy
(74) Attorney, Agent, or Firm—Browning Bushman

(57) ABSTRACT

A safety syringe 10 includes a generally tubular body 14 having a needle end 18 and plunger end 22, needle 38 and retractable needle seat 30, two-way valve 36, plunger 42, stopper 62, piston 52, and rear plunger seal 44. During use, the plunger may be moved to create a vacuum in the plunger. The user then moves the plunger toward the needle end, pressurizing a vial, then pulls backward to a selected position corresponding to the desired volume of fluid to be withdrawn. At the conclusion of the injection stroke, the piston is disengaged from the plunger. The vacuum within the plunger retracts the needle safely into the tubular body.

50 Claims, 13 Drawing Sheets

DISPOSABLE SAFETY SYRINGE

FIELD OF THE INVENTION

The present invention relates generally to syringes and, more particularly, to syringes having retractable needles. The invention specifically relates to a disposable, retractable needle syringe which utilizes created vacuum to automatically retract the needle into the syringe body and thereby prevent the healthcare practitioner from getting stuck by the needle.

BACKGROUND OF THE INVENTION

Hypodermic syringes provide an effective, reliable, and inexpensive way to inject a measured quantity of medicine below the skin. Syringes typically have exposed needles, however, and the ease by which a needle may pierce the skin creates a hazard that the healthcare worker may accidentally be stuck with a needle. The resulting injury could be as simple as a minor skin laceration, or as deadly as an infection from a virus in the patient's blood.

Because syringes are routinely used worldwide, occasional injuries are inevitable when using conventional syringes. Healthcare practitioners are exposed to this danger in routine medical practice. Diabetics, people with arthritis, and others who self-administer daily injections are at risk, as are members of their household. After disposal, conventional syringes may continue to pose a risk to sanitation workers and anyone else who comes in contact with landfills and waste management processes. Some syringes will undoubtedly be disposed of or handled improperly prior to disposal, increasing the chance of injury. Despite their utility, conventional syringes thus clearly pose a danger to healthcare practitioners.

The prior art discloses methods of reducing or eliminating the dangers associated with exposed syringe needles. U.S. Pat. No. 4,908,022 describes a disposable safety syringe having a retractable needle. U.S. Pat. No. 5,885,257 describes a syringe having a spring-loaded, automatically retractable needle. U.S. Pat. No. 5,000,736 describes a syringe having a sealed tubular plunger from which air has been evacuated and a needle releasably attached to the distal end. After the patient is injected, the plunger seal is ruptured and the differential pressure between the vacuum and ambient air causes the needle to retract safely within the syringe body. U.S. Pat. No. 6,193,695 describes a syringe having a sealed portion between the plunger and end cap. As the plunger is pulled away from the needle to fill the syringe, a one-way valve in the sealed portion opens, allowing air to be expelled from the sealed portion. During injection, the plunger is moved toward the needle to expel its contents, the valve closes, and the pressure in the sealed portion decreases. At the end of its stroke, the plunger captures the needle, and the relatively low pressure in the sealed portion causes the plunger and needle to retract into the syringe body. Other patents of interest include U.S. Pat. Nos. 4,425,120; 4,643,200; 4,675,005; 4,692,156; 4,747,830; 4,816,022; and 4,790,822.

Although the prior art has addressed many of the safety problems related to conventional hypodermic syringes, numerous shortcomings remain relating to the cost of manufacturing and the safe use of syringes with retractable needles (safety syringes). Some safety syringes require storage of potential energy, which may be unreliable. For example, sealed vacuum chambers are prone to leakage when the syringe is stored for an extended period. Other safety syringes may have needles which retract a limited distance, with the retracted needle remaining dangerously close to the syringe body opening. Some syringes are shipped and stored with plungers fully extended, increasing their packaged size with a corresponding decrease in the efficiency of shipping and storage. Syringes which utilize springs are costly, and require additional seals to prevent contamination of the fluid drawn into the body of the syringe. Further shortcomings exist in the prior art with regard to manufacturing cost, ease of use, and reliability of safety syringes. A reliable syringe which automatically retracts the needle into the syringe body is sought which overcomes the disadvantages of the prior art.

The present invention surpasses the prior art, offering an improved safety syringe that is both reliable and economical. The retractable-needle or safety syringe of the present invention is relatively simple and convenient to operate.

SUMMARY OF THE INVENTION

The present invention is directed to a safety syringe that retracts its needle into a syringe body to prevent the healthcare practitioner from accidentally getting stuck by the exposed needle. The retractable needle protects various people, including healthcare workers, their patients, and sanitation workers involved with disposal of medical waste. The invention may prevent or reduce injuries ranging from minor skin lacerations to serious contamination by medications, germs, or viruses. The syringe preferably is a disposable, single-use device, and may be available in various sizes and shapes. A syringe according to this invention may also be used in non-medical applications, such as chemical handling processes.

It is an object of the present invention to provide an improved vacuum operated, retractable-needle (safety) syringe. A preferred embodiment includes a selectively retractable needle assembly comprising a needle seat for supporting a needle, and a generally tubular body that serves as a reservoir for injectable or withdrawn fluids. A hollow plunger moves axially within the generally tubular body, and extends from the plunger end of the body for engagement by the health care practitioner. A stopper or other seal between the plunger and tubular body prevents air from passing into or out of the tubular body through the plunger end. As explained below, the hollow plunger is axially moved to draw fluid into the syringe, expel fluid from the syringe into the patient, and create a vacuum within the tubular body, which results in a vacuum in the hollow plunger due to a one-way valve, preferably created by the stopper and ports in the wall of the hollow plunger. A two-way valve, a removable plug, or other controllable plug regulates the flow of liquid and air flowing into and out of the needle end of the tubular body during use. A piston moves axially within the internal chamber in the plunger, and a seat/piston latch selectively engages the needle seat and the piston to withdraw the needle into the hollow plunger due to the created vacuum. Movement of the plunger to the full injection position engages the seat/piston latch, releases the needle seat, and releases the piston from the plunger. The syringe may be distributed and stored in a relatively compact packaged configuration, with the plunger substantially retracted into the tubular body.

To use the syringe, the healthcare practitioner may first pull the plunger from its packaged configuration within the syringe body toward the plunger end of the body. Since the needle end of the body is closed off by a plug, the created vacuum in the body receives air from inside the plunger. The stopper thus also serves as a one way valve to allow air flow from within the plunger to the interior of the body to create a vacuum in the plunger, while preventing reverse flow.

To fill the syringe body, the practitioner may first insert the needle into a vial or other fluid source and move the plunger axially toward the needle end of the tubular body, thereby pressurizing the vial. The practitioner may then pull the plunger axially to a predetermined measurement toward the plunger end of the body to draw fluid into the tubular body. The practitioner may then aspirate the syringe in a conventional manner, eliminating air and any excess liquid. To inject the patient, the practitioner inserts the needle under the skin and forces the plunger toward the needle end of the body to expel the liquid. At the end of the plunger injection stroke, the plunger reaches the full injection position, the seat/piston latch engages the needle seat and the piston, and the piston and needle seat are released, so that the piston and retractable needle assembly now move together with respect to the tubular body. The vacuum within the plunger automatically pulls the piston toward the rear end of the plunger, retracting the needle safely within the plunger and the syringe body.

It is an object of this invention to provide an improved safety syringe. The safety syringe may operate more reliably and consistently than other safety syringes. Because the vacuum in the plunger may be created during the initial movement of the plunger, there is no need for an energy source within the syringe to retract the needle which may degrade or fail prior to use. A related object of the invention is to provide an improved safety syringe which uses a vacuum within the generally tubular body of the syringe created by movement of the plunger to withdraw the needle seat and the attached needle into the generally tubular body.

Another object of the invention is to provide an improved method of using a syringe of the type with a needle seat sealingly engaged within the tubular body for supporting a needle, with the needle seat being releasably retained on the tubular body in an initial position. A practitioner may apply a first axial force to a needle end plugged body to move the plunger to a displaced position, creating a vacuum within the tubular body, which becomes the vacuum within the hollow plunger due to a one-way valve. The practitioner then inserts the needle into the liquid source and withdraws a selected volume of liquid into the tubular body. After aspirating the air, the needle is inserted into a fluid repository, such as a patient, and a second axial force on the plunger is used to discharge liquid from the needle. At the end of the injection stroke, a seat/piston latch connects the needle seat with the piston, the needle seat disengages from the tubular body, and the piston disengages from the plunger so that the released piston and connected needle seat and needle are moved as an assembly to the retracted position within the plunger and also within the tubular body.

It is a feature of the invention that a one-way valve is provided for allowing fluid flow from the interior chamber in the plunger to the throughbore of the generally tubular body, thereby allowing a vacuum within the tubular body to create a vacuum within the plunger, while preventing flow in a reverse direction. In a preferred embodiment, the one-way valve comprises one or more through ports in the plunger, with a stopper normally closing off flow through the ports and opening the ports to create the partial vacuum within the plunger interior chamber.

A further feature of the invention is that movement of the plunger to the full injection position causes the piston to engage the needle seat and release a piston/plunger latch to release the piston from the plunger may include a male and female connector. A shoulder on the piston may pass axially out of a retaining groove in the plunger, thereby releasing the piston from the plunger.

It is also a feature of the invention that the needle seat is retained in its initial position by engagement with the generally tubular body, and that moving the plunger to the fully injected position may cause the plunger to radially expand a portion of the generally tubular body, thereby releasing the needle seat from the tubular body. A related feature of the invention is that a needle seat retainer, which may also serve as a seal between the needle seat and the tubular body, may be engaged by the plunger when in the full injection position to unseal the connection and release the needle seat from the tubular body. In either case, the plunger, when moved to the full injection position, disengages the seat retainer, thereby releasing the needle seat from the body.

A further feature of the invention is the practitioner uses the improved syringe in a manner very similar to operation of a conventional syringe. Graduations on the tubular body increase from the needle end toward the plunger end so that the practitioner withdraws the selected amount of fluid into the syringe, then inserts that fluid into the repository, which causes the needle seat and needle to automatically withdraw within the tubular body.

A feature of the invention is that a simple plug at the needle end of the syringe body may be used as a controllable plug to prevent air from entering the tubular body when the plunger is moved to create a vacuum, and may thereafter be removed to allow fluid communication from outside to within the syringe body. The plug may be provided in the form of a cap which covers or blocks off the needle end of the syringe prior to use, such that the healthcare practitioner creates the vacuum by moving the plunger while a syringe body needle end is plugged by the cap or plug.

A significant advantage of the present invention is that the syringe may be manufactured at a relatively low cost, and accordingly the syringe preferably is a disposable single-use device.

Another significant advantage of the present invention is that the safety syringe may be easily and safely operated by the practitioner.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
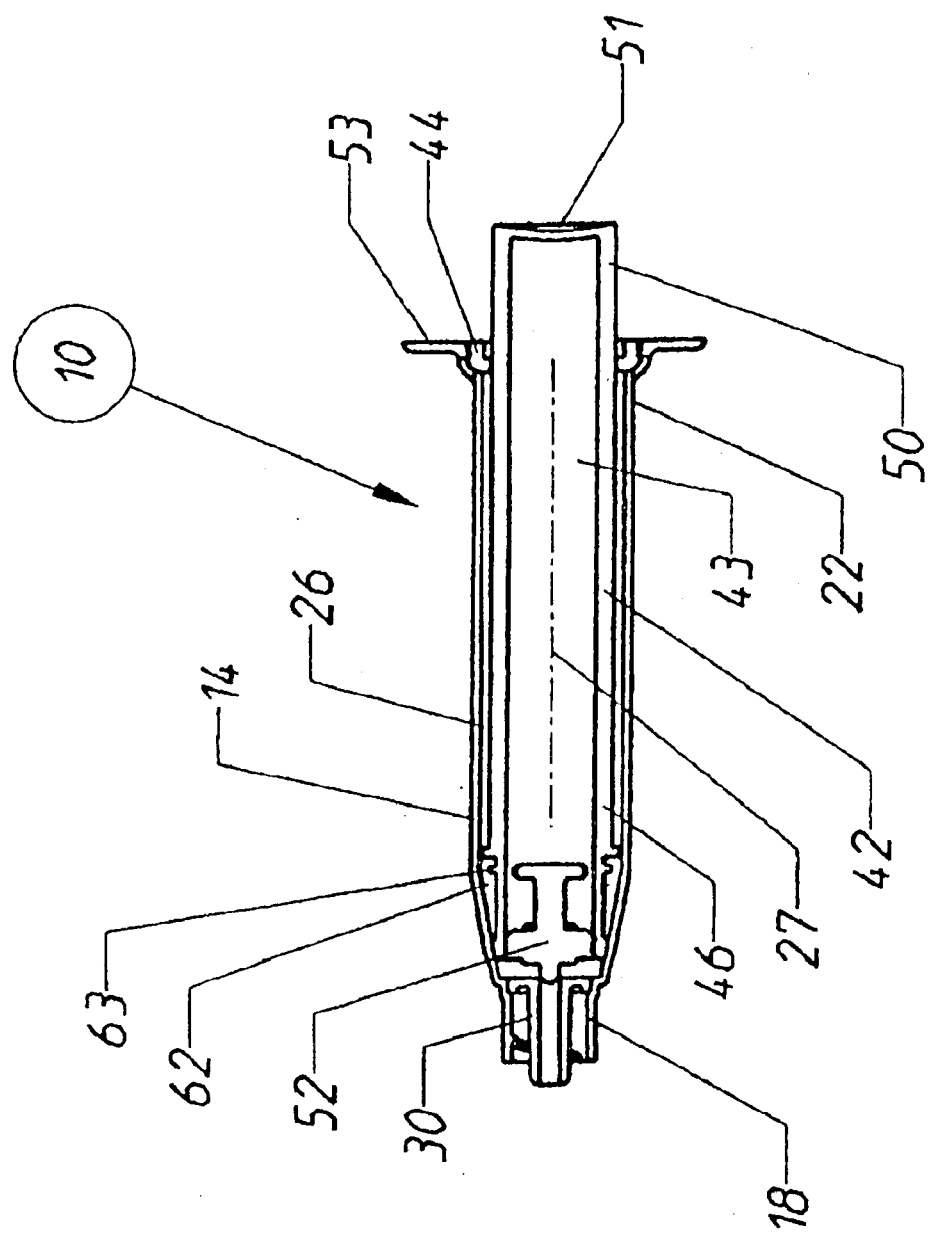
FIG. 1 illustrates in cross-section one embodiment of the safety syringe according to the present invention in an initial, packaged configuration.
Figure 2:
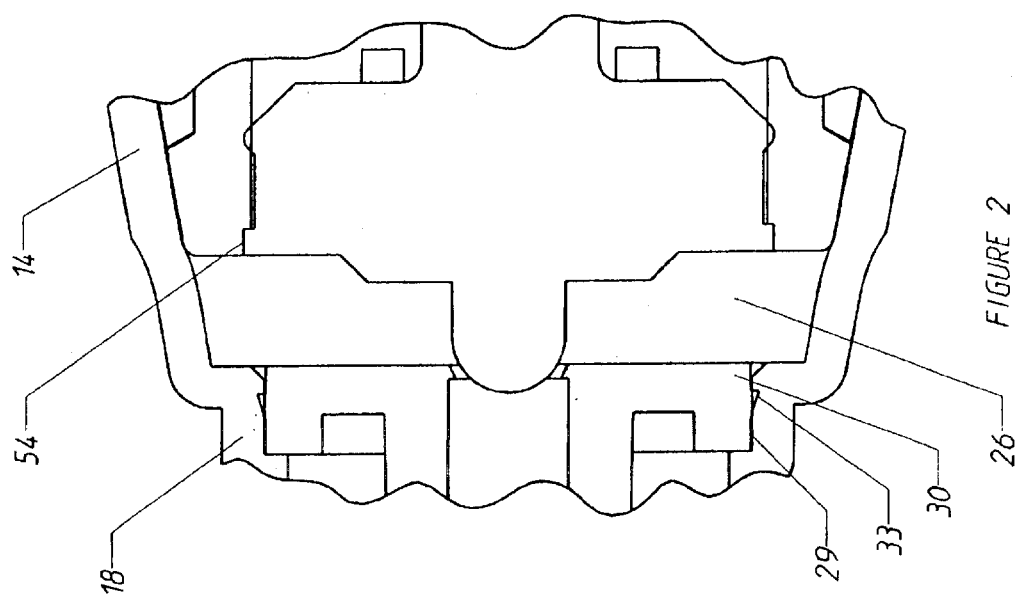
FIG. 2 is an enlarged cross-sectional view of a portion of the syringe shown in FIG. 1.

FIG. 1 shows a syringe 10 in an initial packaged configuration for shipment and storage, with greater detail of the needle seat and piston shown in FIG. 2. A generally tubular body 14, which may house medicine or other liquid during use of the syringe 10, has a needle end 18, an opposing plunger end 22, and a cylindrical throughbore 26 with a central axis 27. The tubular body 14 is preferably plastic, but may comprise other non-porous or leak proof materials.

As shown in FIG. 2, a needle seat 30 is received within the throughbore 26 and at least partially within the reduced diameter portion 29 at the needle end 18 of the tubular body 14. The needle seat 30 may be axially and sealingly attached to the tubular body 14, held in an initial retained position by a seat retainer 33, which may be a generally annular bead on either the needle seat 30 or on the tubular body 14, which engages a similarly configured groove on the other of the needle seat or tubular body. The tubular body sealingly receives the needle seat when in the initial retained position, with the seal being formed by sealing engagement of the components themselves, or by a separate seal between the needle seat and the tubular body. The needle seat 30 is configured for release from the body 14, as discussed below.

Figure 5:
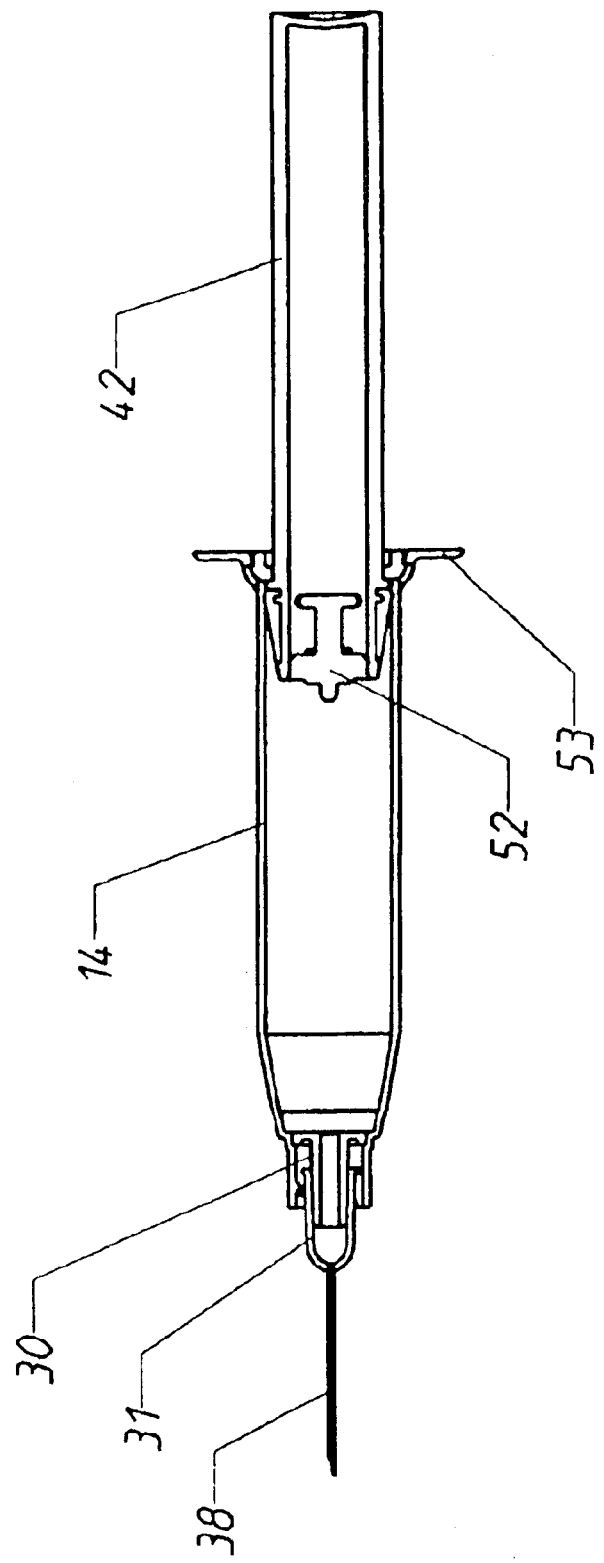
FIG. 5 shows the syringe ready for use with vacuum created and the needle installed on the syringe body.
Figure 6:
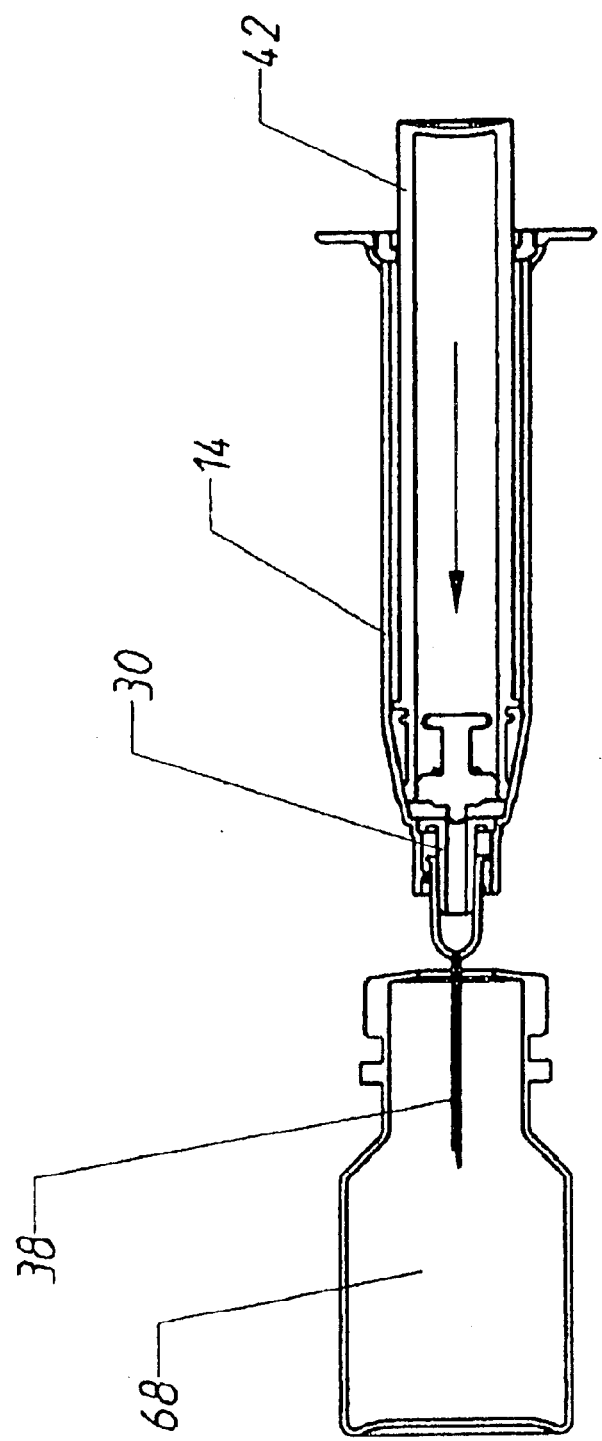
FIG. 6 shows the needle end of the syringe in an ampule, preferably pressuring the ampule.

The needle seat 30 supports a needle 38 (see FIG. 5) which may pierce a layer of skin to transport medicine or other liquid subdermally. The needle seat 30 as shown in FIG. 2 may be configured for attachment to a conventional hub 31 as shown in FIG. 5 by a quarter-turn spiral-lock conventionally used with syringes, with the hub 31 supporting the needle 38 thereon. The needle seat 30 is selectively moveable from the initial retained position (see FIG. 1) to a needle retracted position (see FIG. 11), wherein the attached needle 38 is at least substantially internal to the plunger, and also within the tubular body 14. The seat retainer 33 is shown in the initial retainer position in FIG. 2, in the released position in FIG. 10, and in the retracted position in FIG. 11. In a preferred embodiment, the seat/body retainer 33 as shown in FIG. 6 may comprise a generally circumferential bead on the seat 14 cooperating with an annular groove on the body. Alternatively, the bead could be pivoted on the body, the groove on the needle seat.

Referring again to FIG. 1, the plunger 42 may be used to expel the contents of the syringe 10 toward the needle end 18 and out through the needle 38. The plunger 42 has a needle seat end 46 positioned within the tubular body 14 and an opposed plate end 50 extending from the tubular body 14, with the plunger 42 being axially moveable relative to the tubular body 14. An annular rear stop 44 is preferably provided for preventing the plunger 42 from moving out of the tubular body 14. The plunger has a push/pull plate 51 on the plate end 50. The plunger interior is sealed by the plate 51, and cooperates with the piston 52 to seal an interior chamber 43 in the plunger sized for sealing engagement with the piston 52 to withdraw the piston and the needle into the chamber 43, as discussed further below. The piston 52 is axially retained initially on the plunger 42 by a piston/plunger retainer 54, as shown in FIG. 2. The body 14 may include radially opposing finger tabs 53, as shown in FIG. 1.

The initial configuration of the syringe as shown in FIG. 1 is relatively compact, with the plunger 42 substantially within the tubular body 14. The stopper 62 seals between the body 14 and the plunger 42, and is positioned near the needle end 18 of the body 14.

Figure 3:
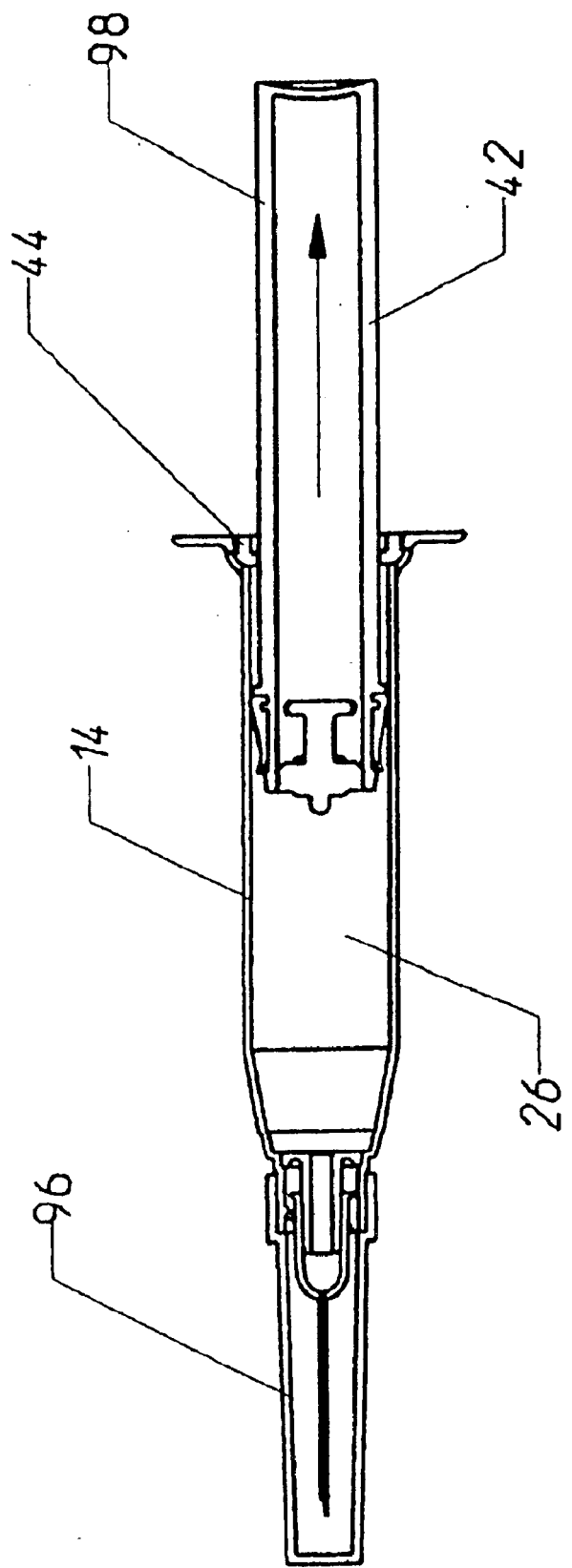
FIG. 3 shows the plunger pulled to create a vacuum in the tubular body.
Figure 13:
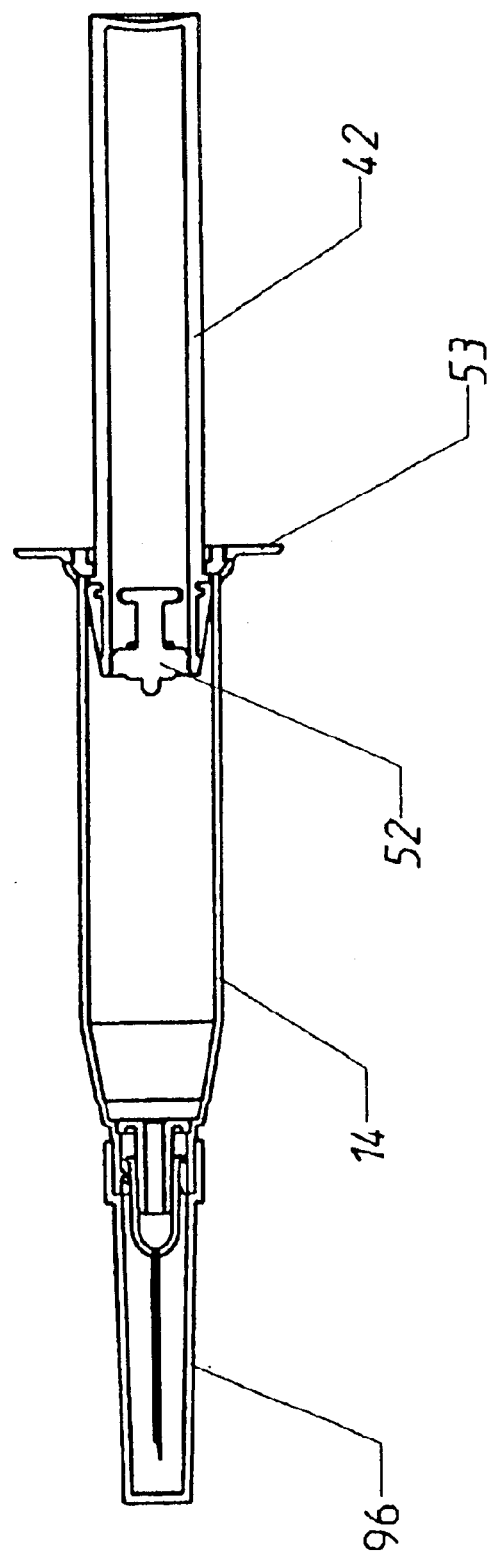
FIG. 13 shows a plug or cap closing off a needle secured to the needle end of the tubular body, with the plunger pulled back to initially create vacuum.

To initiate the filling process, the plunger 42 is first moved into a retracted position (see FIG. 3). Air in the annulus between the body 14 and the plunger passes by the rear stop 44, and out the body 14. A simple plug or cap as shown in FIG. 13 prevents air from entering the tubular body through the needle end during this movement of the plunger, thereby creating a vacuum within the body between the needle seat and the plunger. In one embodiment, the needle is secured in place on the syringe body, and the cap closes off the needle to prevent air from entering the needle. In another embodiment, the cap may close off the needle end of a syringe without a needle mounted thereon, and the cap or plug may then seal directly to the syringe. After the vacuum is created within the syringe, the needle may then be secured to the syringe.

Figure 4:
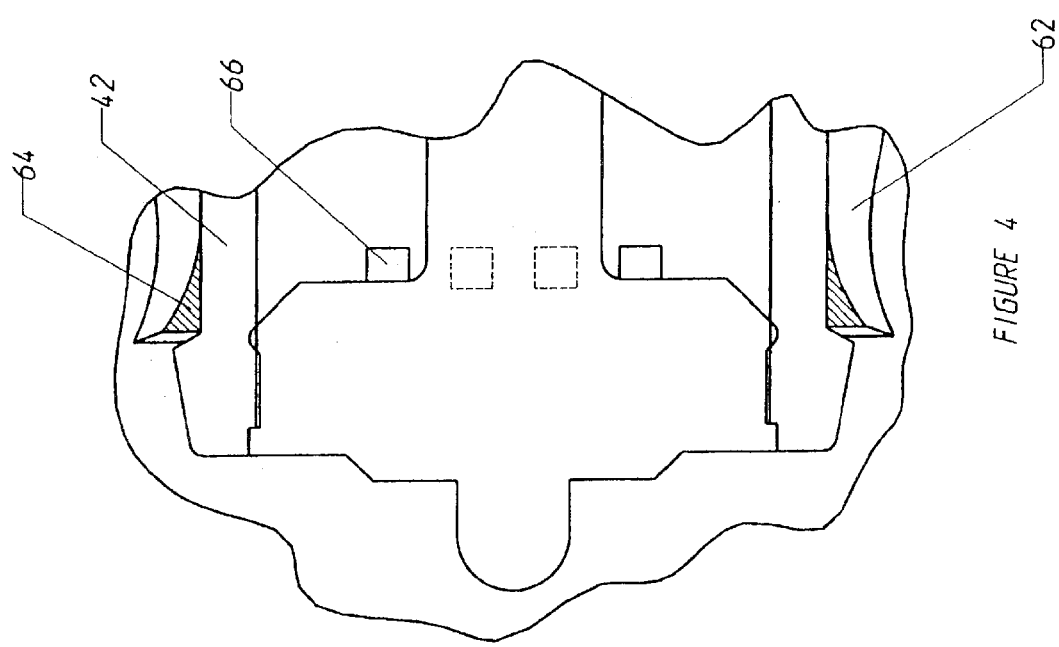
FIG. 4 illustrates in greater detail the ports in the plunger, so that the stopper opens these ports when a partial vacuum exists in the tubular body.

The stopper 62 is axially secured to the plunger 42 by connector 63, and a forward portion 64 of the stopper as shown in FIG. 4 normally covers a plurality of cicumferentially spaced ports 66 in the plunger. A created vacuum in the tubular body and the ambient pressure within the plunger 42 lifts the portion 64 of the stopper out of sealing engagement with the exterior surface of the plunger surrounding the ports 66, thereby allowing air within the plunger 42 to pass into the tubular body 14, so that a partial vacuum exists both within the tubular body 14 and within the plunger 42. A particular feature of the present invention is the use of a stopper 62 which both forms a seal between the plunger and the tubular body and which also acts as a one way valve to allow air to escape from within the plunger through the port 66, while preventing flow from within the tubular body to the interior of the plunger.

Figure 7:
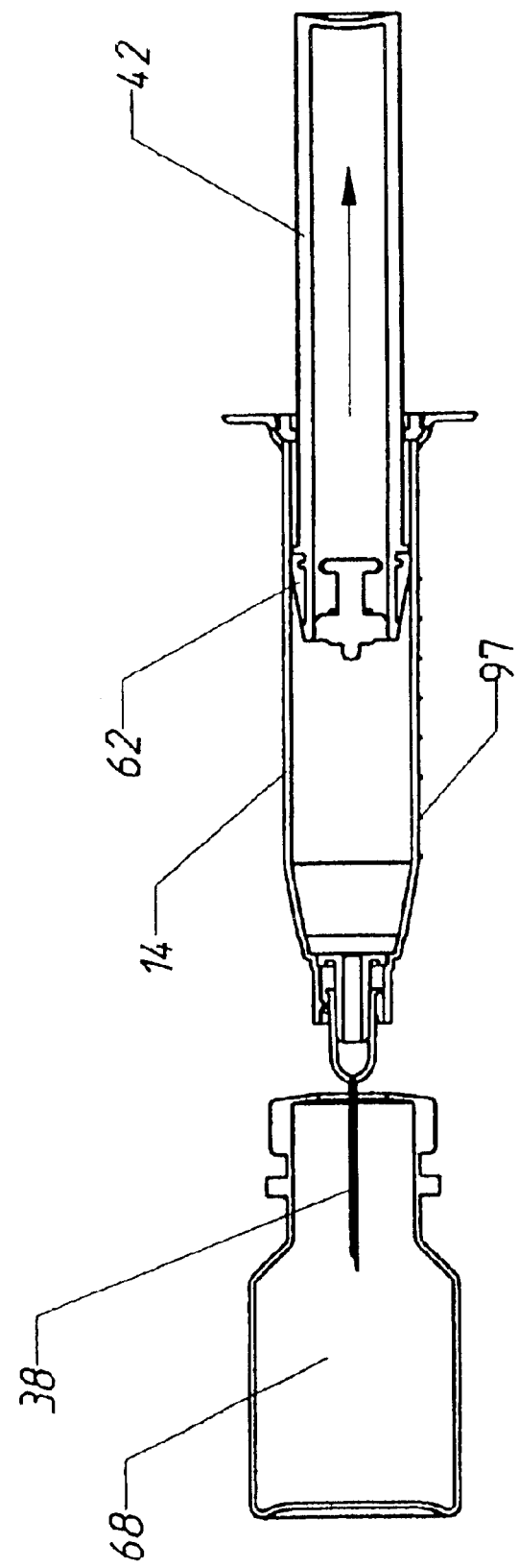
FIG. 7 shows the syringe after the plunger has been moved to a selected, displaced position.

The needle 38, which may then be installed on a syringe or may previously have been secured to the body 14 by the needle seat 30, may then be inserted into the vial or other fluid source 68, then the plunger 42 moved forward to pressurize the vial, as shown in FIG. 6. The plunger 42 may then be moved back toward the plunger end 22 of the tubular body 14 to a liquid withdrawn position, as shown in FIG. 7, drawing a desired volume of liquid from the fluid source 68 into the syringe 10. The stopper 62 is closed since pressure in the body 14 is greater than pressure within the plunger 42. Air may then be aspirated from within the tubular body 14 through the needle 38. The syringe 10 and its contents are now ready for the injection process.

Figure 8:
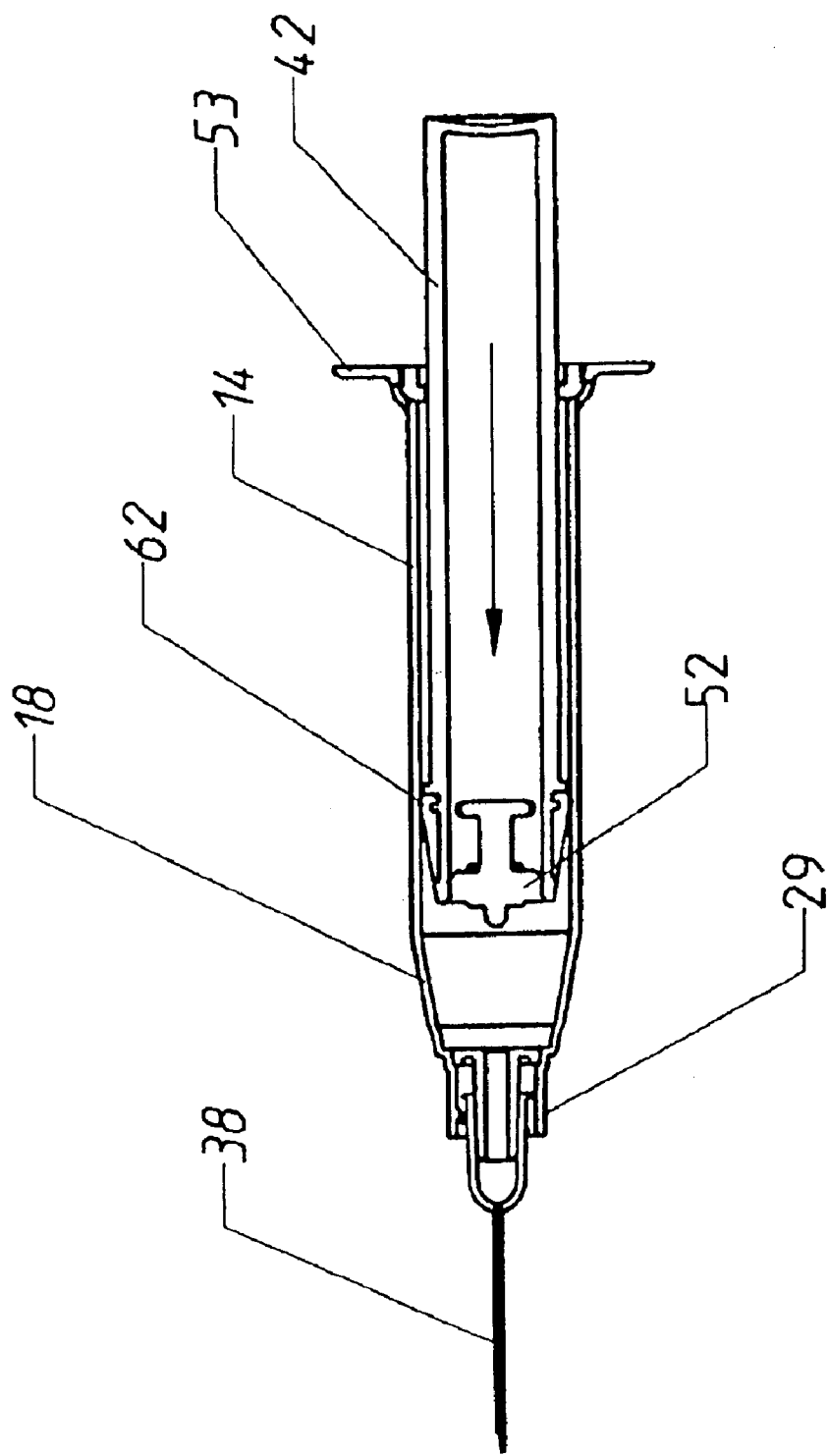
FIG. 8 shows the syringe aspirated for insertion into a patient.
Figure 9:
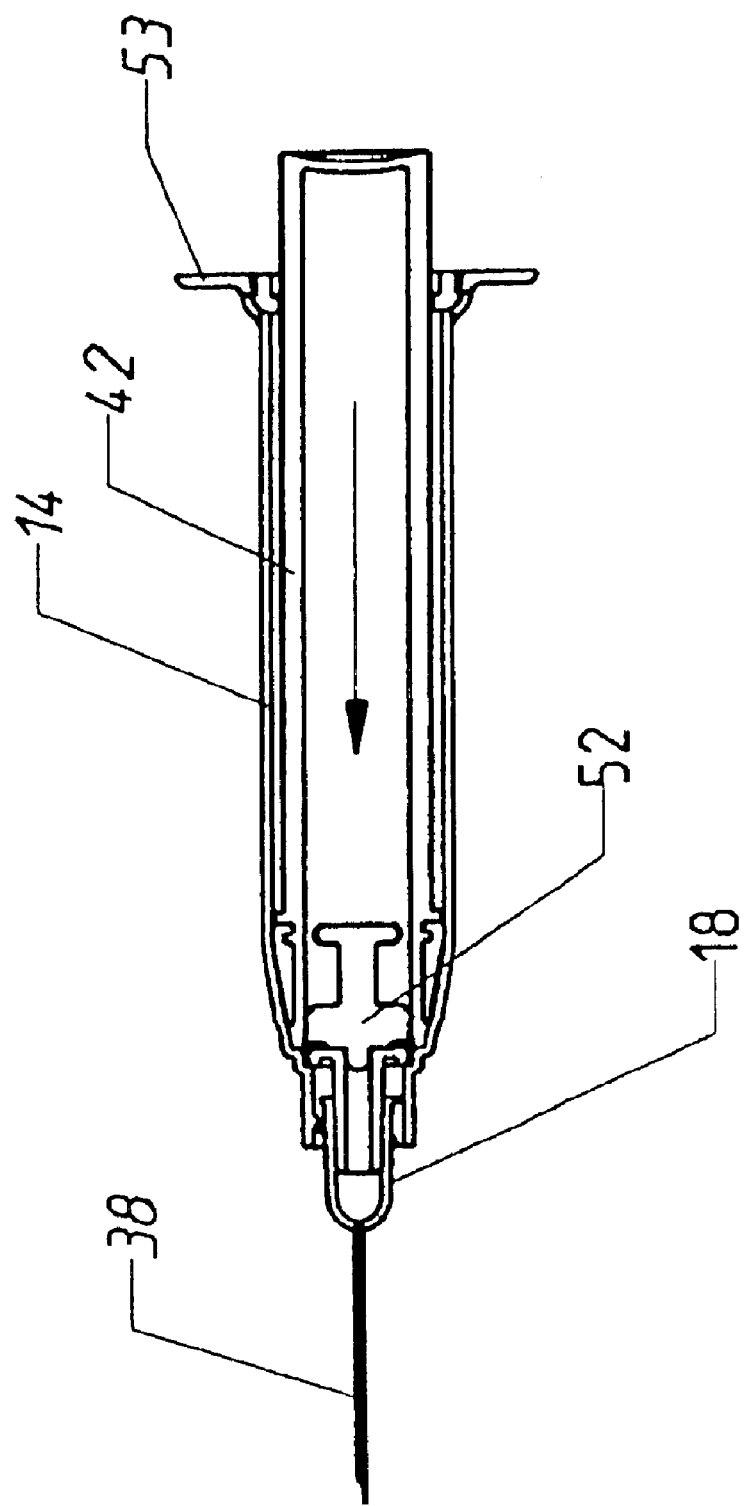
FIG. 9 shows the injection complete, releasing the needle seat and the piston.
Figure 10:
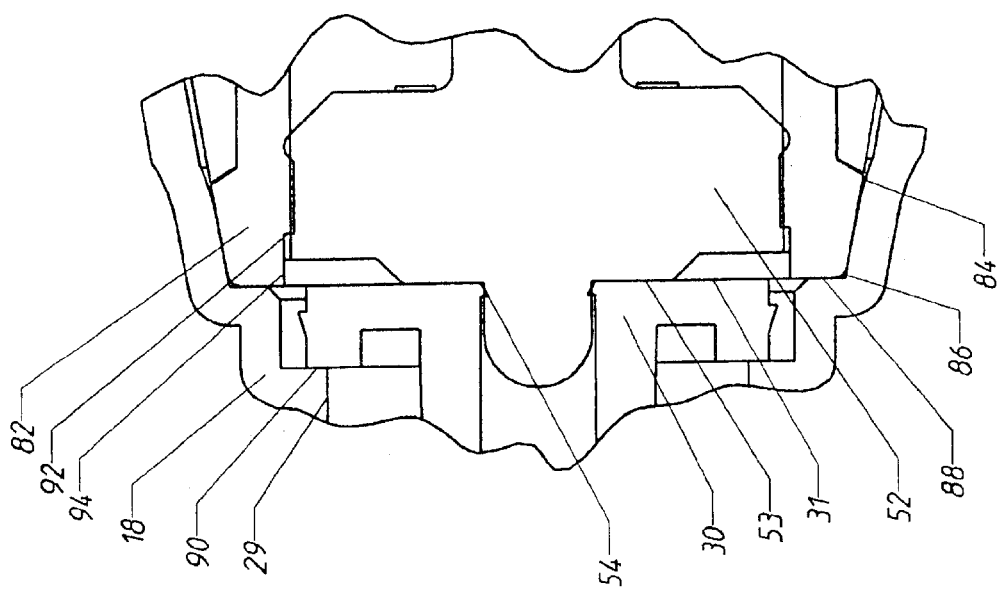
FIG. 10 shows in greater detail the piston and needle seat connection.
Figure 11:
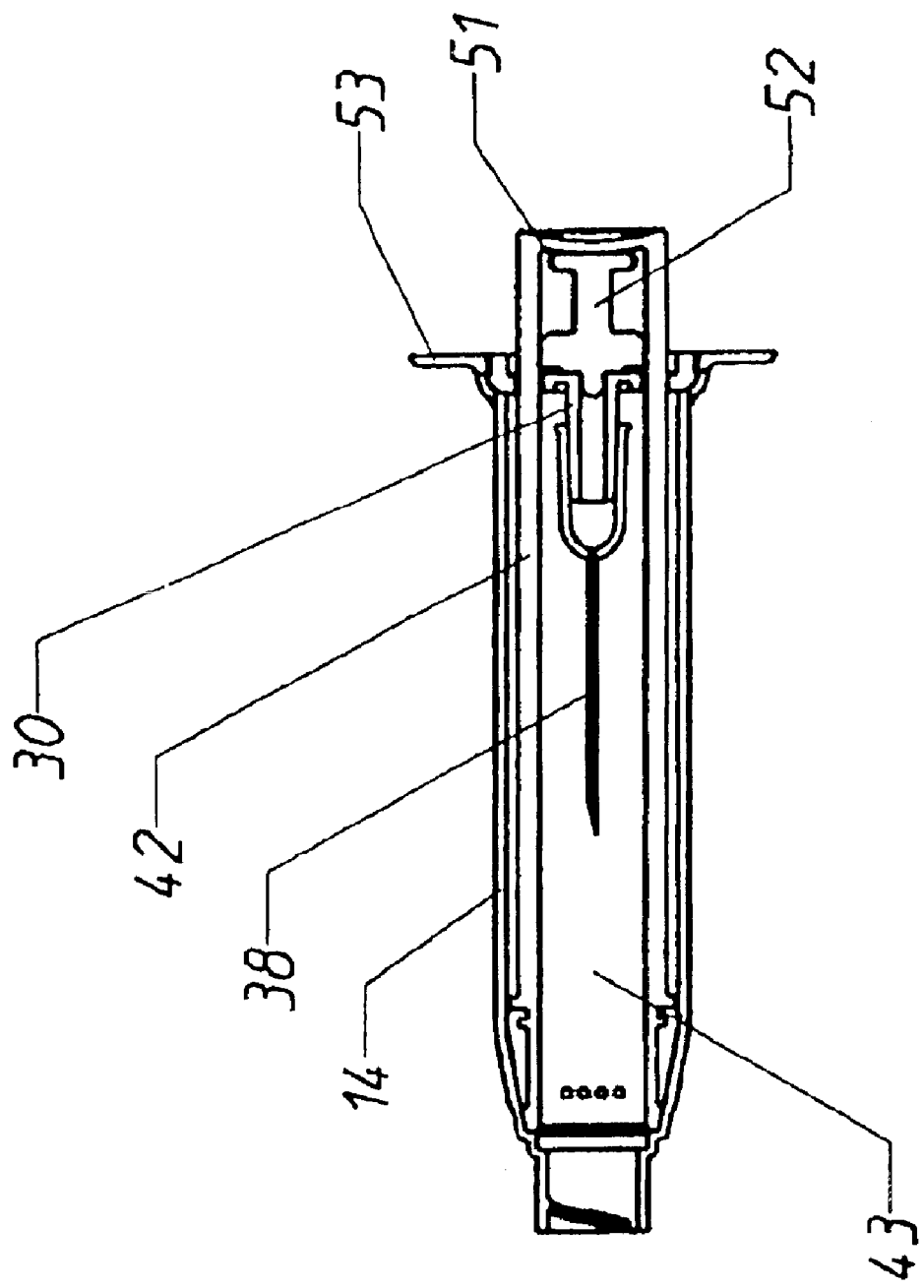
FIG. 11 shows the syringe with its needle in a fully retracted position after use.
Figure 12:
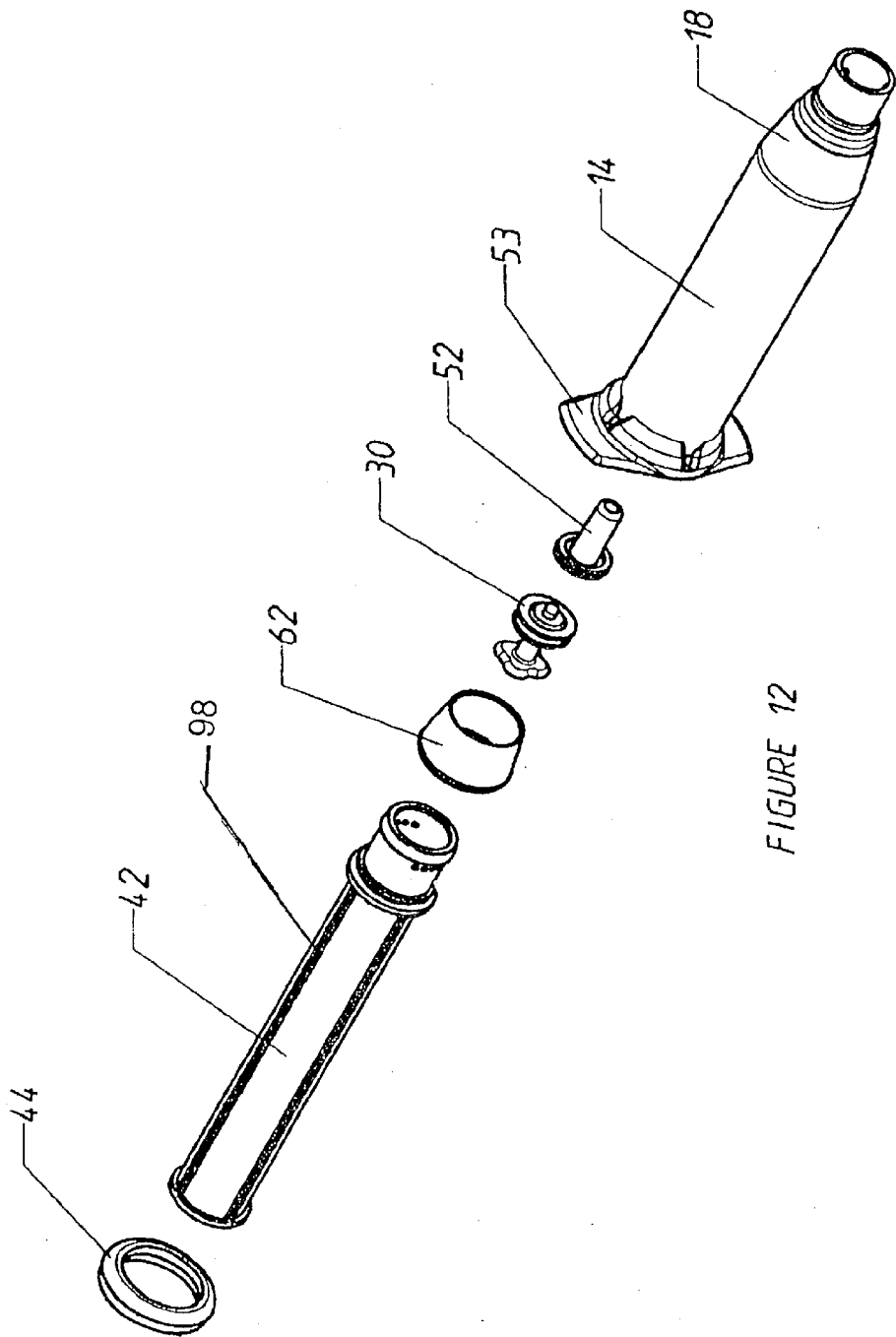
FIG. 12 is an exploded view of an embodiment without a needle mounted on the syringe.

After the needle 38 has been inserted below the skin of a patient, the plunger 42 is forced axially toward the needle end 18, as shown in FIG. 8, and the fluid is forced by the stopper 62 out through the needle 38 and into the patient. At the end of the injection stroke, the piston/seat latch 54 axially connects the piston and the needle seat 30, thereby capturing the needle seat 30, as shown in FIG. 10. At the end of the injection stroke, the needle end 82 of the plunger 42 as shown in FIG. 10 has radially expanded the needle end 18 of the body 14 due to the camming action of surface 84 on the plunger and the mating surface 86 on the body, until the plunger engages the stop surface 88 on the body, which is the complete or full injection position. The expansion of the needle end 18 of the tubular body thus releases the needle seat 30 from the body. At the same time, i.e., at the full injection position, stop surface 53 on the piston 52 has engaged the face 31 of the needle seat 30, as shown in FIG. 10, but forward motion of the needle seat is prevented by the stop surface 90 on the body engaging the needle seat. Accordingly, the piston/plunger retainer 92, which may consist of annular bead or shoulder on the piston 52 which resides within an expanded diameter groove 94 on the plunger 42, is forced rearward with respect to the plunger a slight amount to release the piston/plunger retainer. In this full injection position, a substantial vacuum exists in the plunger relative to the atmospheric pressure or slight positive pressure due to the injection stroke in the tubular body 14 on the opposing side of the piston 52. When the practitioner releases the plunger 42 at the end of its injection stroke, the released piston 52, the disengaged needle seat 30 and attached needle 38 are retracted into a retracted position within the tubular body 14 (see FIG. 11). While the piston is retracted within the plunger, a guide 51 on the piston may be used to retain the piston in axial alignment within the throughbore 43 in the plunger.

Preferably the syringe according to the present invention is a disposable single-use device. Plunger 42 may include a plurality of circumferentially spaced ribs 98 for maintaining proper alignment of the plunger with respect to the body during axial movement or stroking of the plunger. The stopper 62 is secured axially to the plunger, and preferably forms the seal between the body and the plunger and acts as the valve member closing off the ports in the plunger when pressure surrounding the plunger is greater than pressure within the plunger. A preferred piston/seat latch mechanism according to the present invention may include a male member on a piston and a female member on the seat. The male member could alternatively be provided in the seat and the female member on the plunger. The needle may be shipped separately from the syringe, and the needle then attached to the needle seat in a conventional manner. In other embodiments, the needle and needle seat could be formed as a single unit, and the syringe shipped with the needle extending from the tubular body.

Various types of rear stops may be used for preventing the plunger from coming completely out of the tubular body. Various types of plungers and pistons may be used for reliably sealing with the tubular body and the plunger during axial movement of the plunger and the piston. Other types of retainers maybe used for initially retaining the seat 30 in the needle end of the tubular body, and thereafter yielding or releasing the seat once engaged by the plunger to withdraw the needle seat and needle into the tubular body.

The method of the present invention will be readily understood to those skilled in the art in view of the above discussion. The syringe when used has the needle seat sealingly engaging the generally tubular body and retained in an initial retained position. The stopper is provided within the throughbore of a tubular body, and a plunger extends at least partially within the throughbore of the tubular body. A created vacuum in the tubular body 14 when the plunger is moved away from the plugged needle end of the tubular body results in a vacuum within the tubular body 14, which may be substantially equal to the vacuum in the plunger 42 due to the release of air from the plunger by the one-way action of the stopper 62. Once a vacuum is created within the plunger, the plug may be removed from the needle end of the body 14. In one option, the needle 38 and the hub 31 may then be threaded onto the needle seat. The vacuum within the tubular body 14 is intentionally lost, but the vacuum in the plunger 42 is maintained.

A needle may then be inserted into the liquid source, but preferably is inserted into the liquid source prior to applying axial force to the plunger to pressurize the liquid source (typically a vial) with air. A selected volume of liquid from the liquid source is then withdrawn into the tubular body between the needle seat and the stopper while moving the stopper from a selected displaced position to a fluid drawn position. The practitioner conventionally pulls the plunger back to draw fluid into the syringe, as shown in FIG. 7. The tubular body 14 may thus include graduations 97 on an outer surface of the tubular body which increase from the needle end to the plunger end, allowing the healthcare practitioner to withdraw a selected volume of liquid into the throughbore 26 of tubular body 14. After removing the needle from the liquid source and aspirating the air from the syringe, the needle may be inserted into a fluid repository, such as the patient. Thereafter, a second axial force is applied by the practitioner to the plunger to move the plunger toward the needle end of the tubular body to discharge liquid from the tubular body. At the end of the injection stroke, the seat/piston latch is engaged to connect the needle seat with the piston, the piston 52 is released from the plunger 42, and the needle seat 30 is released from the body 14. The second force is then relaxed, allowing the piston 52 and connected needle seat 30 and needle 38 to move from the initial retained position to the needle seat retracted position.

As discussed above, a removable plug may serve to prevent entry of air into the syringe from the needle end of the tubular body. FIG. 13 discloses a cap or plug 96 which may seal over the needle secured to the syringe during manufacture, as discussed above, so that the user initially pulls the plunger to create the vacuum as shown in FIG. 13, so that the cap 96 thereafter may be removed from the needle and the syringe and be discarded. In a preferred embodiment, the needle is securely mounted on the syringe body at this time, although in alternate embodiments the syringe and plug could be provided separately from the needle.

The cap as discussed above is a preferred way to plug or seal the needle end of the tubular body until the vacuum has been created within the plunger. Various types of plugs may be used for this purpose. For example, a female plug may be used to slide over a male member on the needle end of the plunger body. An alternative plug may act as a male member for closing off the entry port in the needle end of the tubular body. As a further alternative, a pressure responsive flow valve or a pressure release valve may be used for closing off the entry port in the needle end of the tubular body.

As discussed above, the stopper acts as both a seal between the plunger and the syringe body and cooperates with ports in the plunger to act as a one-way valve. In a less desired alternative, the stopper may be used as only a seal, and another mechanism used as a one-way valve. A separate one-way valve might be provided, for example, within a passageway in the piston, allowing opening of the valve to obtain the vacuum within the plunger, but then automatically closing the valve once air enters the needle end of the syringe body and pressure in the syringe is greater than pressure within the plunger. As discussed above, the stopper is preferably axially secured to and moveable with the plunger, although limited axial movement between the stopper and the plunger would be permissible in some applications. Various types and configurations of pistons may be used for sealing with the interior of the plunger to withdraw the piston and the needle into the plunger.

According to the preferred embodiment discussed above, the plunger is moved to the full injection position, thereby initially engaging the piston with the needle seat. At substantially the same time, the seat/piston latch axially connects the needle seat with a piston, the needle seat is released from engagement with the tubular body, and the piston is released for moving with the captured needle and the needle seat to a retracted position within the plunger and within the tubular body. These three actions preferably occur simultaneously, or may occur in any sequence desired by the syringe manufacturer. The primary point is that once the plunger is moved to the full injection position, the force supplied by the user to the plunger may be released, and automatically reactions occur which cause the needle to be safely retracted within the syringe body.

A particular feature of the present invention is that the syringe has a relatively low cost, and the needle is reliably drawn into the tubular body after use. The syringe according to the present invention is particularly well suited for use when injecting a small quantity of fluid, e.g., less than 10 cc, and in some applications the tubular body may hold less than a maximum of about 5 cc.

In addition to medical applications, the syringe may be used in other nonmedical applications. For example, if using the syringe for chemical extraction and disposal, rather than injection into a patient, the syringe 10 may be used to inject fluid into a different type of fluid receptacle, such as an open flask or other chemical handling media. The needle 38 may be designed accordingly to accommodate the desired process. For example, whereas a human patient may require use of a narrow, sharp needle, chemical extraction and disposal may require a larger needle to extract larger volumes of chemical fluids, or fluids with a higher viscosity.

It may be appreciated that changes to the details of the illustrated embodiments and systems disclosed are possible without departing from the spirit of the invention. While preferred and alternative embodiments of the present invention have been described in detail, it is apparent that further modifications and adaptations of the preferred and alternative embodiments may occur to those skilled in the art. However, it is to be expressly understood that such modifications and adaptations are within the spirit and scope of the present invention, as set forth in the following claims.

What is claimed is:

1. A syringe for retracting a needle supported on a needle seat, comprising:
    a generally tubular body having a needle end and an opposing plunger end, the tubular body having an internal throughbore extending between the needle end and the opposing plunger end, the tubular body sealing receiving the needle seat therein;
    a seat/body retainer adjacent the needle end of the tubular body for initially attaching the needle seat to the generally tubular body, the needle seat being selectively moveable within the tubular body from an initial retained position to a needle seat retracted position;
    a plunger having an interior chamber therein and a needle seat end positioned within the internal throughbore of the generally tubular body, the plunger being moveable within the throughbore of the tubular body;
    a stopper for sealed engagement between the generally tubular body and the plunger;
    a piston selectively moveable between an initial retained position adjacent the needle seat end of the plunger and a piston retracted position within the plunger;
    a one-way valve allowing flow from the interior chamber in the plunger to the throughbore in the generally tubular body while preventing fluid flow from the throughbore in the generally tubular body to the interior chamber in the plunger;
    a seat/piston latch for selective engagement of the needle seat with the piston; and
    a controllable plug selectively preventing fluid from entering the tubular body through the needle end when in a closed position.

2. A syringe as defined in claim 1, wherein the one-way valve comprises one or more through ports in the plunger, and the stopper is moveable relative to the one or more ports between a closed position for closing off flow through the ports and an open position for opening the ports to create a partial vacuum within the plunger interior chamber.

3. A syringe as defined in claim 2, wherein the stopper automatically moves radially outward to the open position in response to reduced pressure in the tubular body throughbore compared to pressure in the interior chamber in the plunger.

4. A syringe as defined in claim 1, wherein the piston is selectively retained in the initial retained position by a piston/plunger retainer, and the piston engages the needle seat to disengage the piston/plunger retainer and release the piston to move away from the needle seat end of the plunger.

5. A syringe as defined in claim 1, wherein:
    the seat/piston latch includes one of a male connector and a female connector secured to the plunger and the other of the male connector and the female connector secured to the piston.

6. The syringe as defined in claim 1, further comprising:
    graduations on the, tubular body increasing from the needle end toward the plunger end.

7. A syringe as defined in claim 1, further comprising:
    a plate secured to a plate end of the plunger for applying an axial force to the plunger.

8. A syringe as defined in claim 1, wherein the stopper is axially secured to and moveable with the plunger.

9. A syringe as defined in claim 1, further comprising:
    a stop secured to the tubular body for preventing the plunger from coming fully out of the tubular body.

10. A syringe as defined in claim 1, wherein the controllable plug is a manually removed plug.

11. A syringe as defined in claim 10, wherein the removable plug seals a needle supported on the tubular body end, and is manually removed subsequent to creating a vacuum with the plunger.

12. A syringe as defined in claim 10, wherein the removable plug seals the needle end of the tubular body and is manually removed subsequent to creating a vacuum within the plunger.

13. A syringe as defined in claim 1, wherein movement of the plunger to an injection position expands a portion of a generally tubular body to release the seat/body retainer and the needle seat from the tubular body.

14. A syringe as defined in claim 1, wherein a seal between the needle seat and the tubular body retains the needle seat in the initial retained position, and movement of the plunger to an injection position moves the seal such that the needle seat is released from the generally tubular body.

15. A syringe for retracting a needle supported on a needle seat, comprising:
    a generally tubular body having a needle end and an opposing plunger end, the tubular body having an internal throughbore extending between the needle end and the opposing plunger end, the tubular body sealing receiving the needle seat therein;

a seat/body retainer adjacent the needle end of the tubular body for initially attaching the needle seat to the generally tubular body, the needle seat being selectively moveable within the tubular body from an initial retained position to a needle seat retracted position;

a plunger having an interior chamber therein and a needle seat end positioned within the internal throughbore of the generally tubular body, the plunger being sealed to the tubular body and moveable within the throughbore of the tubular body;

a piston selectively moveable between an initial retained position adjacent the needle seat end of the plunger and a piston retracted position within the plungers the piston being selectively retained in the initial retained position by a piston/plunger retainer, and the piston engages the needle seat to disengage the piston/plunger retainer and release the piston to move away from the needle seat end of the plunger;

a one-way valve allowing flow from the interior chamber in the plunger to the throughbore in the generally tubular body while preventing fluid flow from the throughbore in the generally tubular body to the interior chamber in the plunger, a seat/piston latch for selective engagement of the needle seat with the piston; and a controllable plug selectively preventing fluid from entering the tubular body through the needle end when in a closed position.

16. A syringe is defined in claim 15, wherein the piston/plunger retainer includes a shoulder on one of the piston and the plunger for positioning within a groove on the other of the piston and the plunger when the piston is in the initial retained position.

17. A syringe as defined in claim 15, wherein the one-way valve comprises one or more through ports in the plunger, and a stopper which seals between the body and the plunger is moveable relative to the one or more ports between a closed position for closing off flow through the ports and an open position for opening the ports to create a partial vacuum within the plunger interior chamber.

18. A syringe as defined in claim 15, wherein the seat/piston latch includes one of a male connector and a female connector secured to the plunger and the other of the male connector and the female connector secured to the piston.

19. A syringe as defined in claim 15, wherein the controllable plug seals a needle supported on the tubular body and is manually removed subsequent to creating a vacuum within the plunger.

20. A syringe as defined in claim 15, wherein movement of the plunger to an injection position expands a portion of a generally tubular body to release the seat/body retainer and the needle seat from the tubular body.

21. A syringe as defined in claim 15, wherein a seal between the needle seat and the tubular body retains the needle seat in the initial retained position, and movement of the plunger to an injection position moves the seal such that the needle seat is released from the generally tubular body.

22. A syringe for retracting a needle supported on a needle seat, comprising:

a generally tubular body having a needle end and an opposing plunger end, the tubular body having an internal throughbore extending between the needle end and the opposing plunger end, the tubular body sealing receiving the needle seat therein;

a seat/body retainer adjacent the needle end of the tubular body for initially attaching the needle seat to the generally tubular body, the needle seat being selectively moveable within the tubular body from an initial retained position to a needle seat retracted position;

a plunger having an interior chamber therein and a needle seat end positioned within the internal throughbore of the generally tubular body, the plunger being sealed to the tubular body and moveable within the throughbore of the tubular body;

a piston selectively moveable between an initial retained position adjacent to the needle seat end of the plunger and a piston retracted position within the plunger;

a one-way valve allowing flow from the interior chamber in the plunger to the throughbore in the generally tubular body while preventing fluid flow from the throughbore in the generally tubular body to the interior chamber in the plunger;

a seat/piston latch including one of a male connector and a female connector secured to the plunger and the other of the male connector and the female connector secured to the piston for selective engagement of the needle seat with the piston; and a controllable plug selectively preventing fluid from entering the tubular body through the needle end when in a closed position.

23. A syringe as defined in claim 22, wherein the one-way valve comprises one or more through ports in the plunger, and a stopper which seals between the body and the plunger is moveable relative to the one or more ports between a closed position for closing off flow through the ports and an open position for opening the ports to create a partial vacuum within the plunger interior chamber.

24. A syringe as defined in claim 22, further comprising:

graduations on the tubular body increasing from the needle end toward the plunger end; and a plate secured to a plate end of the plunger for applying an axial force to the plunger.

25. A syringe as defined in claim 22, wherein movement of the plunger to an injection position expands a portion of a generally tubular body to release the seat/body retainer and the needle seat from the tubular body.

26. A syringe as defined in claim 22, wherein a seal between the needle seat and the tubular body retains the needle seat in the initial retained position, and movement of the plunger to an injection position moves the seal such that the needle seat is released from the generally tubular body.

27. A method of using a syringe with a needle seat supporting a needle retractable in a generally tubular body having an internal throughbore extending between a needle end and an opposing plunger end, the method comprising:

sealingly engaging the needle seat with the generally tubular body, the needle seat being selectively movable from an initial retained position to a needle seat retracted position;

releasably retaining the needle seat in the initial retained position;

axially securing a stopper to a plunger within the throughbore of the tubular body;

positioning the plunger at least partially within the throughbore of the tubular body, the plunger including an internal chamber therein;

positioning a piston within the plunger moveable from an initial position in the needle end of the plunger to a retracted position within the internal chamber in the plunger;

providing a one-way valve between the internal chamber in the plunger and the throughbore of the generally tubular body;

plugging the needle seat end of the tubular body;
applying a first axial force to move the plunger from an initial position in the opposing plunger end of the tubular body to a selected displaced position, thereby creating a vacuum within the tubular body between needle end of the tubular body and the stopper and opening the one-way valve to obtain a vacuum within the plunger;
removing the plug in the needle seat end of the tubular body; inserting a needle into a liquid source;
withdrawing a selected volume of liquid from the liquid source through the needle and into the tubular body between the needle seat and the stopper while moving the plunger to a fluid drawn position;
thereafter inserting the needle into a fluid repository; thereafter applying a second axial force to the plunger to move the stopper toward the needle end of the tubular body while discharging liquid from within the tubular body;
engaging a seat/piston latch to axially connect the needle seat with the piston; and
relaxing the second force to disengage the needle seat from the generally tubular body and move the piston and the connected needle seat from the initial retained position to the needle seat retracted position.

28. A method as defined in claim 27, wherein the needle is inserted into the liquid source before moving the plunger to the displaced position, thereby pressurizing the liquid source while the plunger moves to the displaced position.

29. A method as defined in claim 27, wherein providing a one way valve includes providing one or more ports in the plunger, the stopper covering the one or more ports to close the valve when pressure within the body is greater than pressure within the plunger.

30. A method as defined in claim 27, wherein movement of the plunger to a full injection position releases the piston from a retained position on the plunger.

31. A method as defined in claim 27, further comprising:
engaging the piston with the needle seat to release the piston from the plunger to move the piston axially away from the needle end of the plunger.

32. A method as defined in claim 27, wherein a wrapper encloses the tubular body to plug the needle end of the tubular body, and moving the plunger to create the vacuum opens the wrapper to unplug the needle end of the tubular body.

33. A method as defined in claim 27, further comprising:
providing graduations on the tubular body increasing from the needle end toward the plunger end.

34. A method as defined in claim 27, further comprising:
moving the plunger to an injection position such that the plunger expands a portion of the generally tubular body to release the needle seat.

35. A method as defined in claim 27, further comprising:
moving the plunger to an injection position such that the plunger moves a seal between the seat and the tubular body to release the needle seat.

36. A method of using a syringe with a needle seat supporting a needle retractable in a generally tubular body having an internal throughbore extending between a needle end and an opposing plunger end, the method comprising:
sealingly engaging the needle seat with the generally tubular body;
the needle seat being selectively movable from an initial retained position to a needle seat retracted position;
releasably retaining the needle seat in the initial retained position;
axially securing a stopper to a plunger within the throughbore of the tubular body;
positioning the plunger at least partially within the throughbore of the tubular body, the plunger including an internal chamber therein;
positioning a piston within the plunger moveable from an initial position in the needle end of the plunger to a retracted position within the internal chamber in the plunger, wherein the piston is selectively retained in the initial retained position by a piston/plunger retainer, and the piston engages the needle seat to disengage the piston/plunger retainer and release the piston to move away from the needle seat end of the plunger;
providing a one-way valve between the internal chamber in the plunger and the throughbore of the generally tubular body;
plugging the needle seat end of the tubular body;
applying a first axial force to move the plunger from an initial position in the opposing plunger end of the tubular body to a selected displaced position, thereby creating a vacuum within the tubular body between needle end of the tubular body and the stopper and opening the one-way valve to obtain a vacuum within the plunger;
removing the plug in the needle seat end of the tubular body; inserting a needle into a liquid source;
withdrawing a selected volume of liquid from the liquid source through the needle and into the tubular body between the needle seat and the stopper while moving the plunger to a fluid drawn position;
thereafter inserting the needle into a fluid repository;
thereafter applying a second axial force to the plunger to move the stopper toward the needle end of the tubular body while discharging liquid from within the tubular body;
engaging a seat/piston latch to axially connect the needle seat with the piston; and
relaxing the second force to disengage the needle seat from the generally tubular body and move the piston and the connected needle seat from the initial retained position to the needle seat retracted position.

37. A method as defined in claim 36, wherein the needle is inserted into the liquid source before moving the plunger to the displaced position, thereby pressurizing the liquid source while the plunger moves to the displaced position.

38. A method as defined in claim 36, wherein providing a one way valve includes providing one or more ports in the plunger, the stopper covering the one or more ports to close the valve when pressure within the body is greater than pressure within the plunger.

39. A method as defined in claim 36, further comprising:
providing graduations on the tubular body increasing from the needle end toward the plunger end.

40. A method as defined in claim 36, further comprising:
moving the plunger to an injection position such that the plunger expands a portion of the generally tubular body to release the needle seat.

41. A method as defined in claim 36, wherein plugging the needle seat end of the tubular includes supporting a needle on the tubular body and plugging the needle with a plug, and removing the plug in the needle seat end of the tubular body includes removing the plug from the needle.

42. A method of using a syringe with a needle seat supporting a needle retractable in a generally tubular body having an internal throughbore extending between a needle end and an opposing plunger end, the method comprising:

sealingly engaging the needle seat with the generally tubular body, the needle seat being selectively movable from an initial retained position to a needle seat retracted position;

releasably retaining the needle seat in the initial retained position;

axially securing a stopper to a plunger within the throughbore of the tubular body; positioning the plunger at least partially within the throughbore of the tubular body, the plunger including an internal chamber therein;

positioning a piston within the plunger moveable from an initial position in the needle end of the plunger to a retracted position within the internal chamber in the plunger;

providing a one-way valve between the internal chamber in the plunger and the throughbore of the generally tubular body;

plugging the needle seat end of the tubular body;

applying a first axial force to move the plunger from an initial position in the opposing plunger end of the tubular body to a selected displaced position, thereby creating a vacuum within the tubular body between needle end of the tubular body and the stopper and opening the one-way valve to obtain a vacuum within the plunger;

removing the plug in the needle seat end of the tubular body, thereby closing the one-way valve;

inserting a needle into a liquid source;

withdrawing a selected volume of liquid from the liquid source through the needle and into the tubular body between the needle seat and the stopper while moving the plunger to a fluid drawn position;

thereafter inserting the needle into a fluid repository;

thereafter applying a second axial force to the plunger to move the stopper toward the needle end of the tubular body while discharging liquid from within the tubular body;

engaging a male member on one of the piston and the needle seat with a female member on the other of the piston and the needle seat to axially connect the needle seat with the piston; and relaxing the second force to disengage the needle seat from the generally tubular body and automatically move the piston and the connected needle seat from the initial retained position to the needle seat retracted position.

43. A method as defined in claim 42, wherein the needle is inserted into the liquid source before moving the plunger to the displaced position, thereby pressurizing the liquid source while the plunger moves to the displaced position.

44. A method as defined in claim 42, wherein plugging the needle seat end of the tubular includes supporting a needle on the tubular body and plugging the needle with a plug, and removing the plug in the needle seat end of the tubular body includes removing the plug from the needle.

45. A method as defined in claim 42, wherein movement of the plunger to a full injection position releases the piston from the retained position on the plunger.

46. A method as defined in claim 42, wherein providing a one way valve includes providing one or more ports in the plunger, the stopper covering the one or more ports to close the valve when pressure within the body is greater than pressure within the plunger.

47. A method as defined in claim 42, further comprising:
providing graduations on the tubular body increasing from the needle end toward the plunger end.

48. A method as defined in claim 42, further comprising:
moving the plunger to an injection position such that the plunger expands a portion of the generally tubular body to release the needle seat.

49. A method as defined in claim 42, further comprising:
moving the plunger to an injection piston such that the plunger moves a seal between the seat and the tubular body to release the needle seat.

50. A method as defined in claim 42, further comprising:
engaging the piston with the needle seat to release the piston from the plunger to move the piston axially away from the needle end of the plunger.

* * * * *